(12) United States Patent
Philbrick

(10) Patent No.: US 12,277,820 B1
(45) Date of Patent: Apr. 15, 2025

(54) SECURITY AND SAFETY CONFIGURATIONS FOR DRONE DELIVERY

(71) Applicant: United Services Automobile Association (USAA), San Antonio, TX (US)

(72) Inventor: Ashley Raine Philbrick, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 18/439,416

(22) Filed: Feb. 12, 2024

Related U.S. Application Data

(63) Continuation of application No. 17/707,460, filed on Mar. 29, 2022, now Pat. No. 11,935,347.

(Continued)

(51) Int. Cl.
*G07C 9/23* (2020.01)
*A61L 2/10* (2006.01)
*A61L 2/24* (2006.01)
*A61L 2/28* (2006.01)
*B64C 39/02* (2023.01)

(Continued)

(52) U.S. Cl.
CPC ............... *G07C 9/23* (2020.01); *A61L 2/10* (2013.01); *A61L 2/24* (2013.01); *A61L 2/28* (2013.01); *B64C 39/024* (2013.01); *G05D 1/104* (2013.01); *G06N 20/00* (2019.01); *G06Q 10/0832* (2013.01); *G06Q 10/08355* (2013.01); *G06V 10/70* (2022.01); *G06V 20/52* (2022.01); *G07C 9/00896* (2013.01); *A61L 2202/122* (2013.01); *A61L 2202/14* (2013.01);

(Continued)

(58) Field of Classification Search
CPC .............. G07C 9/23; G07C 9/00896; G07C 2009/0092; A61L 2/10; A61L 2/24; A61L 2/28; A61L 2202/122; A61L 2202/14; A61L 2202/16; B64C 39/024; G05D 1/104; G06N 20/00; G06Q 10/0832; G06Q 10/08355; G06V 10/70; G06V 20/52; B64U 2101/60
USPC ....................................... 340/5.54
See application file for complete search history.

(56) References Cited

U.S. PATENT DOCUMENTS 9,066,987 B2 * 6/2015 Bettles ...................... A61L 2/10
9,216,857 B1 * 12/2015 Kalyan ................ G06Q 10/087

(Continued)

*Primary Examiner* — Nam V Nguyen
(74) *Attorney, Agent, or Firm* — Potomac Law Group, PLLC; Dannon G. Allbee

(57) ABSTRACT

Embodiments described herein disclose methods and systems for community item distribution. In some implementations, the community item distribution system includes a platform for users to post information regarding items they want to share with the community. The community item distribution system can categorize the information and establish donation parameters for the shared items. The donation parameters can include where and when items can be donated or retrieved, what types of items can be donated, and who can request the donated items. In some cases, the community item distribution system can generate a user interface listing the available items that users can request. Upon request of an item, the community item distribution system can schedule a drone to transport the item, in a secured container with ultraviolet lights to disinfect the item, from the storage location to the delivery location.

20 Claims, 10 Drawing Sheets

Related U.S. Application Data

(60) Provisional application No. 63/168,497, filed on Mar. 31, 2021.

(51) Int. Cl.
*B64U 101/60* (2023.01)
*G05D 1/00* (2024.01)
*G06N 20/00* (2019.01)
*G06Q 10/0832* (2023.01)
*G06Q 10/0835* (2023.01)
*G06V 10/70* (2022.01)
*G06V 20/52* (2022.01)
*G07C 9/00* (2020.01)

(52) U.S. Cl.
CPC ....... *A61L 2202/16* (2013.01); *B64U 2101/60* (2023.01); *G07C 2009/0092* (2013.01)

(56) References Cited

U.S. PATENT DOCUMENTS

| | | | |
|---|---|---|---|
| 9,878,061 B2 * | 1/2018 | Shur | F25D 11/00 |
| 10,010,636 B2 * | 7/2018 | Henniges | A61L 2/28 |
| 10,586,464 B2 * | 3/2020 | Dupray | G08G 5/0008 |
| 10,621,539 B2 | 4/2020 | Matula et al. | |
| 10,621,543 B2 * | 4/2020 | Gupte | B65G 1/1371 |
| 10,664,788 B2 | 5/2020 | Hansmann et al. | |
| 11,068,838 B1 * | 7/2021 | Cougar | G06Q 10/0833 |
| 11,164,140 B2 | 11/2021 | Konanur et al. | |
| 11,447,245 B2 | 9/2022 | Neubecker et al. | |
| 11,475,778 B1 | 10/2022 | Kaneria et al. | |
| 11,769,106 B2 | 9/2023 | Newell et al. | |
| 11,771,786 B1 * | 10/2023 | Glidden | A61L 2/04 |
| | | | 422/3 |
| 11,854,108 B2 * | 12/2023 | Farris | B64U 70/90 |
| 11,883,552 B2 * | 1/2024 | Wei | B65B 55/02 |
| 11,947,365 B2 * | 4/2024 | Polega | G05D 1/686 |
| 11,992,566 B2 * | 5/2024 | Gillespie | A61L 2/10 |
| 2012/0027640 A1 * | 2/2012 | Betz | A61L 2/07 |
| | | | 422/26 |
| 2014/0081445 A1 | 3/2014 | Villamar | |
| 2014/0254896 A1 * | 9/2014 | Zhou | G06Q 20/3829 |
| | | | 705/16 |
| 2015/0120094 A1 * | 4/2015 | Kimchi | G05D 1/00 |
| | | | 701/3 |
| 2016/0033966 A1 | 2/2016 | Farris et al. | |
| 2016/0068264 A1 * | 3/2016 | Ganesh | G06Q 30/0641 |
| | | | 701/4 |
| 2019/0114564 A1 * | 4/2019 | Ferguson | G06Q 10/06315 |
| 2019/0263521 A1 | 8/2019 | O'Brien et al. | |
| 2021/0097481 A1 * | 4/2021 | Salter | A61L 2/10 |
| 2022/0142388 A1 | 5/2022 | Foster | |

* cited by examiner

SECURITY AND SAFETY CONFIGURATIONS FOR DRONE DELIVERY

CROSS-REFERENCE TO RELATED APPLICATIONS

This application is a continuation of U.S. application Ser. No. 17/707,460, titled "SECURITY AND SAFETY CONFIGURATIONS FOR DRONE DELIVERY," filed on Mar. 29, 2022, now U.S. Pat. No. 11,935,347 issued on Mar. 19, 2024, which claims priority to U.S. Provisional Application No. 63/168,497, titled "SECURITY AND SAFETY CONFIGURATIONS FOR DRONE DELIVERY," filed on Mar. 31, 2021, both of which are incorporated by reference in their entirety.

TECHNICAL FIELD

The present disclosure is directed to a system for distributing community items to users via a drone, which can have security enhancements.

BACKGROUND

Users may possess items (e.g., food, clothing, emergency supplies, etc.) that they want to share with others rather than disposing of them. However, it can be difficult to determine what to do with such items. Currently, users can deliver the items to donation centers where the items are sorted and placed for sale in a store or given out to those in need. In some cases, the users can post the items on a website for potential buyers to view. In the event of a purchase, the seller must ship the item to the buyer or arrange for the buyer to pick-up the item.

Various drones exist that can deliver items. However, due to legal restrictions, costs, and privacy concerns around drones, it may not be economical for users to own and operate personal drones to deliver packages. In some cases, items can be stolen from delivery drones or the items can be contaminated (e.g., carry a disease or virus).

BRIEF DESCRIPTION OF THE DRAWINGS

The techniques introduced here may be better understood by referring to the following Detailed Description in conjunction with the accompanying drawings, in which like reference numerals indicate identical or functionally similar elements.

DETAILED DESCRIPTION

Figure 1:
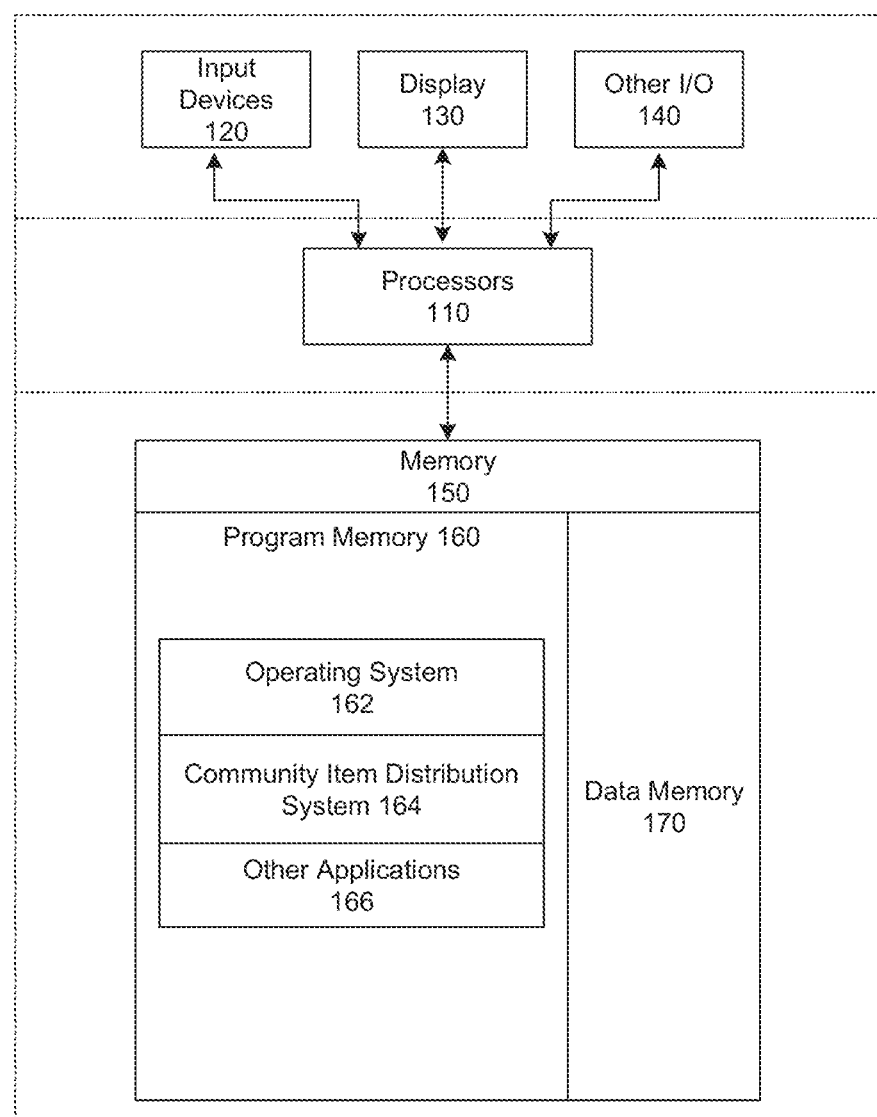
FIG. 1 is a block diagram illustrating an overview of devices on which some implementations can operate.

Aspects of the present disclosure are directed to collecting and distributing community items via a drone. While it's common for people to donate or share items (e.g., food, clothing, tools, emergency supplies, etc.), it can be difficult to gather, store, and coordinate the delivery of the items. Thus, a community item distribution system is needed to coordinate the storage and distribution of items to users. In some implementations, the community item distribution system includes a platform for users to post information (e.g., item descriptions, images of item, etc.) regarding items they want to share with the community. The community item distribution system can categorize the information about the shared items, such as types of items, the locations of items, or expiration dates of items. In some cases, the community item distribution system can establish donation parameters for the shared items. The donation parameters can include where and when items can be donated/retrieved, categorizations of the items, expiration date, weight, size dimensions, storage locations of the items, the types of items that can be shared, the frequency that a user can request items, or the delivery distance (e.g., radius of 2 miles) from the recipient. Additional details on receiving and cataloging shared items are provided below in relation to FIG. 4A.

A recipient user can enter her information (e.g., delivery address, phone number, email, name, military status, employment status, etc.) into the platform (e.g., website or application) and the community item distribution system can select available items based on the user information, such as a delivery location. In some cases, the community item distribution system can generate a user interface listing the available items to the user. Upon request (e.g., by loading a website or app) the community item distribution system can display the available items for a recipient user to view, select, and request for delivery. Upon receiving a selection of an item from a recipient user, the system can schedule a drone (flying or land-based) to transport the item from the storage location to the delivery location of the recipient. The drone can transport the item in a secured container attached to the drone. A user at the storage location can access the secured container and place the item inside. Upon the delivery, the recipient user can enter an access code to retrieve the item from the secured container. Additional details on receiving an item selection and delivery are provided below in relation to FIGS. 4B and 5.

The drones can receive delivery information from the community item distribution system which includes a route to a pickup (storage) location, a routes from the pickup location to a drop-off (delivery) location, and security procedures for the delivery. In some implementations, the drone can disinfect the items prior to delivering the items to the recipient, in which case the drone can also receive a disinfectant schedule for the items. As examples, the secure container can contain various disinfecting systems to reduce the risk of contagion on the items, such as one or more ultraviolet (UV) lights, ozone generators, chemical dispensers (e.g., with alcohol vapor or other disinfecting chemicals).

The drone can apply a disinfectant schedule while it transports the items to a delivery location. The disinfectant schedule can be determined by mapping features of the items, such as their size, type (e.g., food, clothing, electronics), surface materials, etc., to aspects of the disinfecting process such as duration or intensity of UV light to apply, amount of ozone, alcohol vapor, or other chemical disinfectant to apply, etc. Additional details on drones disinfecting items are provided below in relation to FIG. 6.

Methods and systems disclosed herein can provide technical advantages over conventional item sharing systems. Various embodiments employ the technical means of automated management and the distribution of items to provide users with a greater ability to share items in a safe manner. For example, the community item distribution system can provide one or more of the following technological improvements when coordinating computing systems to: 1) set-up a community item service; 2) monitor the viability of the items and manage the categorized items; 3) disinfect the items before a designated recipient receives the item; and 4) implement item delivery, e.g., to provide items via a drone to users.

Some existing systems can deliver items via a drone, yet these existing systems only provide the items and do not manage a supply of community items and coordinate delivery from multiple sources to variable delivery locations, much less do existing systems disinfect the items before delivering the items to the recipient while securing them in transport. The community item distribution system and processes described herein provides a solution for sharing community items by categorizing information of the items, establishing item donation parameters, receiving requests for the categorized items, scheduling a drone to deliver the requested item, and disinfecting the item prior to delivering the item. For example, the community item distribution system can ensure that the user receives her requested item in a safe manner (e.g., disinfected from bacteria). Also, the community item distribution system allows items to be donated without the supplying user having to leave her home. This alleviates both an issue with storing donated items (as items can be kept by the supplying user until a drone arrives to take the items to a recipient) while also increasing the likelihood that items will be donated by eliminating the hurdle of supplying users having to travel to a particular drop-off location. Furthermore, the disclosed community item distribution system can allow sharing with at-risk individuals who may otherwise not be able to obtain such items. For example, many homeless people have access to mobile phones with location information, and the community item distribution system can allow these people to select food and other necessary items and have them delivered to the user's device location, without having to go to a food kitchen or donation center, which may be too difficult or costly for many people.

Several implementations are discussed below in more detail in reference to the figures. FIG. 1 is a block diagram illustrating an overview of devices on which some implementations of the disclosed technology can operate. The devices can comprise hardware components of a device 100 that support a community item distribution system. Device 100 can include one or more input devices 120 that provide input to the Processor(s) 110 (e.g. CPU(s), GPU(s), HPU(s), etc.), notifying it of actions. The actions can be mediated by a hardware controller that interprets the signals received from the input device and communicates the information to the processors 110 using a communication protocol. Input devices 120 include, for example, a mouse, a keyboard, a touchscreen, an infrared sensor, a touchpad, a wearable input device, a camera- or image-based input device, a microphone, or other user input devices.

Processors 110 can be a single processing unit or multiple processing units in a device or distributed across multiple devices. Processors 110 can be coupled to other hardware devices, for example, with the use of a bus, such as a PCI bus or SCSI bus. The processors 110 can communicate with a hardware controller for devices, such as for a display 130. Display 130 can be used to display text and graphics. In some implementations, display 130 provides graphical and textual visual feedback to a user. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network card, video card, audio card, USB, firewire or other external device, camera, printer, speakers, CD-ROM drive, DVD drive, disk drive, or Blu-Ray device.

In some implementations, the device 100 also includes a communication device capable of communicating wirelessly or wire-based with a network node. The communication device can communicate with another device or a server through a network using, for example, TCP/IP protocols. Device 100 can utilize the communication device to distribute operations across multiple network devices.

The processors 110 can have access to a memory 150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 150 can include program memory 160 that stores programs and software, such as an operating system 162, community item distribution system 164, and other application programs 166. Memory 150 can also include data memory 170, item data, drone data, categorization data, location data, user data, machine learning data, identity data, security data, user interface data, donation parameter data, disinfection schedule data, route data, flight data, configuration data, settings, user options or preferences, etc., which can be provided to the program memory 160 or any element of the device 100.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2:
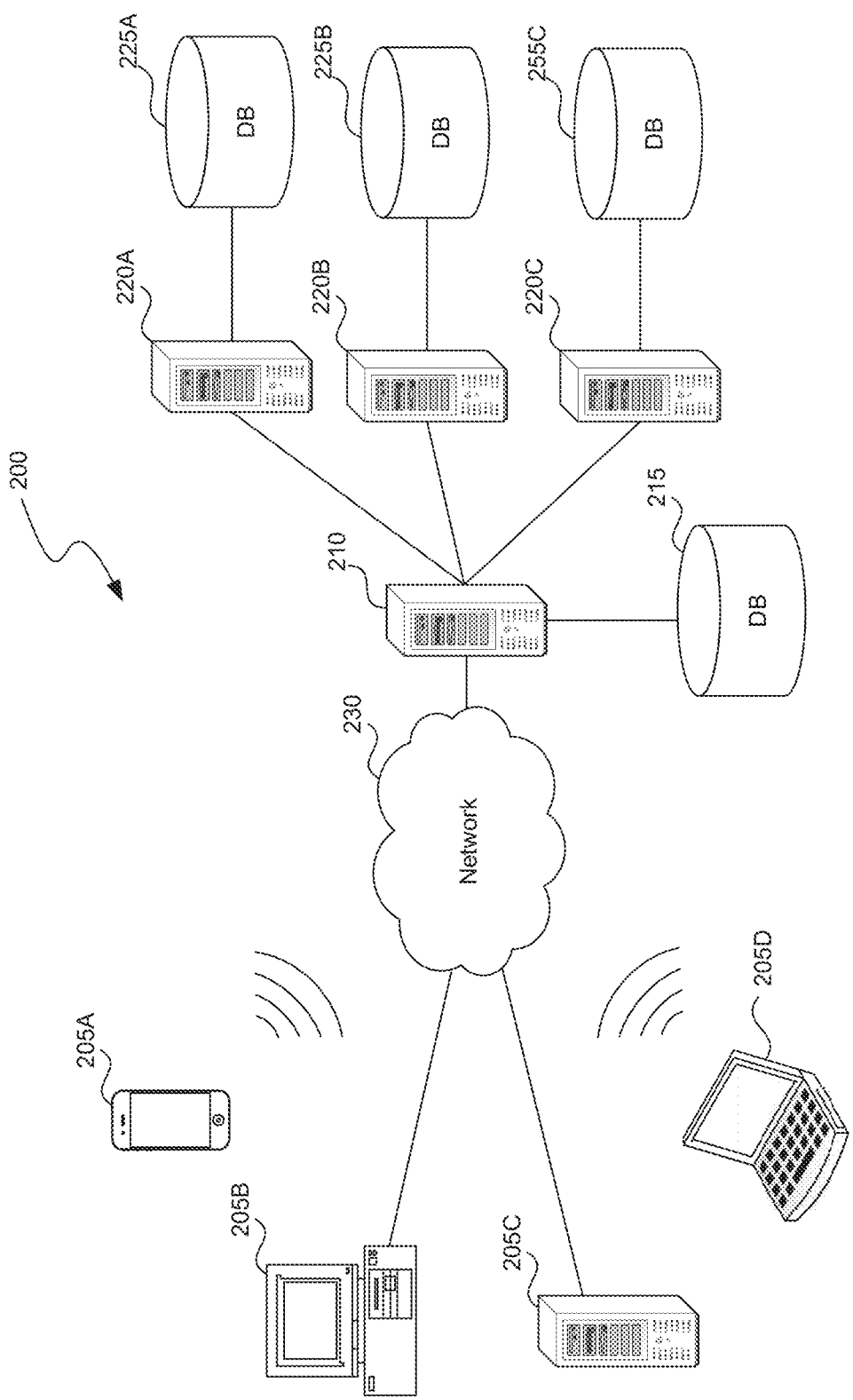
FIG. 2 is a block diagram illustrating an overview of an environment in which some implementations can operate.

FIG. 2 is a block diagram illustrating an overview of an environment 200 in which some implementations of the disclosed technology can operate. Environment 200 can include one or more client computing devices 205A-D, examples of which can include device 100. Client computing devices 205 can operate in a networked environment using logical connections through network 230 to one or more remote computers, such as a server computing device.

In some implementations, server 210 can be an edge server which receives client requests and coordinates fulfillment of those requests through other servers, such as servers 220A-C. Server computing devices 210 and 220 can comprise computing systems, such as device 100. Though each server computing device 210 and 220 is displayed logically as a single server, server computing devices can each be a distributed computing environment encompassing multiple computing devices located at the same or at geographically disparate physical locations. In some implementations, each server 220 corresponds to a group of servers.

Client computing devices 205 and server computing devices 210 and 220 can each act as a server or client to other server/client devices. Server 210 can connect to a database 215. Servers 220A-C can each connect to a corresponding database 225A-C. As discussed above, each server 220 can correspond to a group of servers, and each of these servers can share a database or can have their own database. Databases 215 and 225 can warehouse (e.g. store) information such as item data, drone data, categorization data, location data, user data, machine learning data, identity data, security data, user interface data, donation parameter data, disinfection schedule data, route data, flight data, or configuration data. Though databases 215 and 225 are displayed logically as single units, databases 215 and 225 can each be a distributed computing environment encompassing multiple computing devices, can be located within their corresponding server, or can be located at the same or at geographically disparate physical locations.

Network 230 can be a local area network (LAN) or a wide area network (WAN), but can also be other wired or wireless networks. Network 230 may be the Internet or some other public or private network. Client computing devices 205 can be connected to network 230 through a network interface, such as by wired or wireless communication. While the connections between server 210 and servers 220 are shown as separate connections, these connections can be any kind of local, wide area, wired, or wireless network, including network 230 or a separate public or private network.

Figure 3:
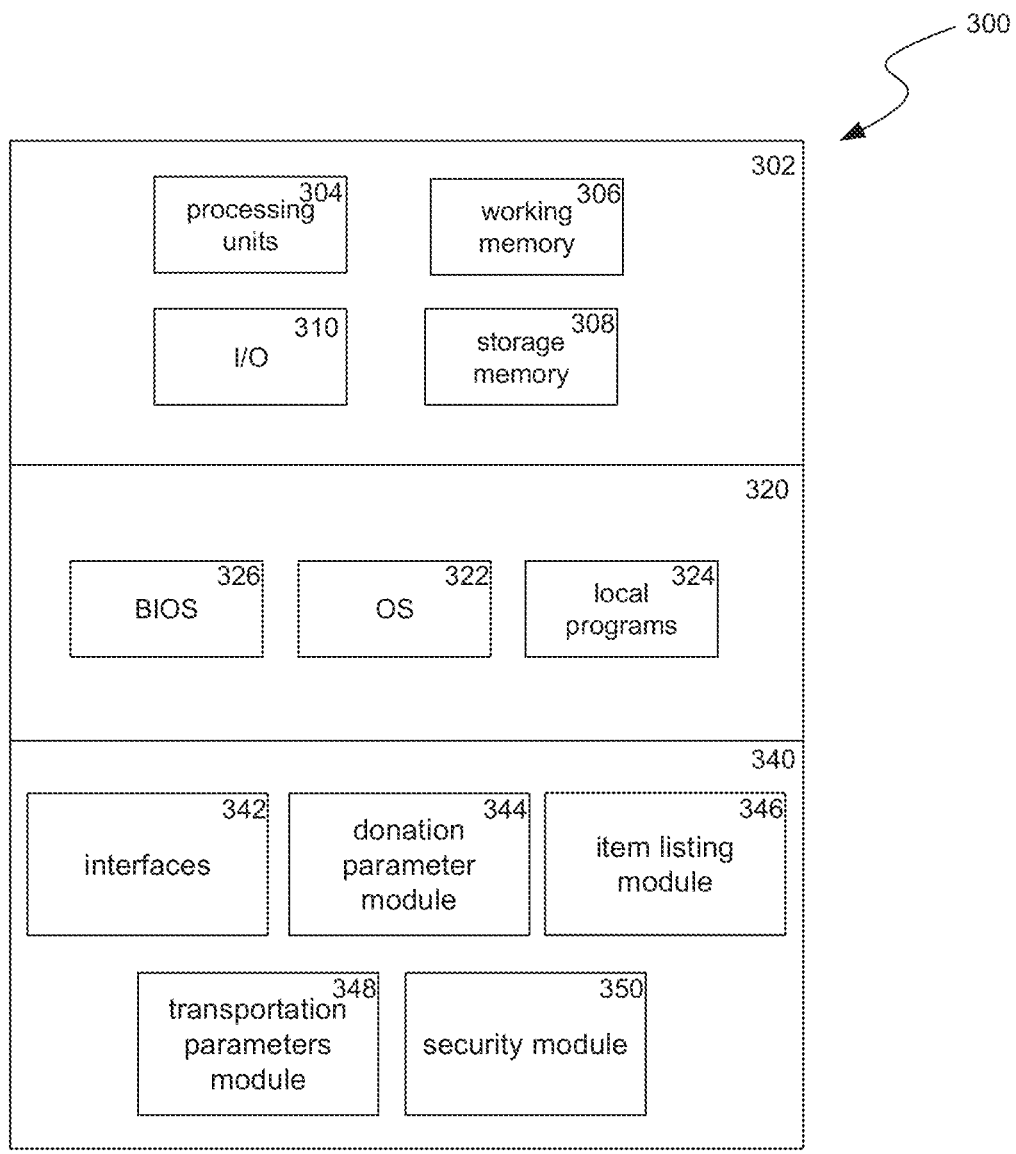
FIG. 3 is a block diagram illustrating components which, in some implementations, can be used in a system employing the disclosed technology.

FIG. 3 is a block diagram illustrating components 300 which, in some implementations, can be used in a system employing the disclosed technology. The components 300 include hardware 302, general software 320, and specialized components 340. As discussed above, a system implementing the disclosed technology can use various hardware including processing units 304 (e.g. CPUs, GPUs, APUs, etc.), working memory 306, storage memory 308 (local storage or as an interface to remote storage, such as storage 215 or 225), and input and output devices 310. In various implementations, storage memory 308 can be one or more of: local devices, interfaces to remote storage devices, or combinations thereof. For example, storage memory 308 can be a set of one or more hard drives (e.g. a redundant array of independent disks (RAID)) accessible through a system bus or can be a cloud storage provider or other network storage accessible via one or more communications networks (e.g. a network accessible storage (NAS) device, such as storage 215 or storage provided through another server 220). Components 300 can be implemented in a client computing device such as client computing devices 205 or on a server computing device, such as server computing device 210 or 220.

General software 320 can include various applications including an operating system 322, local programs 324, and a basic input output system (BIOS) 326. Specialized components 340 can be subcomponents of a general software application 320, such as local programs 324. Specialized components 340 can include donation parameter module 344, item listing module 346, transportation parameters module 348, and security module 350, and components which can be used for providing user interfaces, transferring data, and controlling the specialized components, such as interfaces 342. In some implementations, components 300 can be in a computing system that is distributed across multiple computing devices or can be an interface to a server-based application executing one or more of specialized components 340. Although depicted as separate components, specialized components 340 may be logical or other nonphysical differentiations of functions and/or may be submodules or code-blocks of one or more applications.

In some implementations, the donation parameter module 344 is configured to establish item donation parameters for donated items. The donation parameter module 344 can specify when and where an item can be provided. In some cases, the donation parameters are based on categories (e.g., food, clothing, tools, emergency supplies, etc.), expiration dates, weight, size dimensions, and the storage location of the of the items. The donation parameters can be used to select a drone to deliver the item to the delivery location. Additional details on donation parameters are provided below in relation to block 408 of FIG. 4.

In some implementations, the item listing module 346 is configured to generate a user interface listing items available to a user. The item listing module 346 can select the items to display based on the delivery location associated with the user, item donation points associated with the user, or the status of the user (e.g., employed, homeless, serving in the military, household income, etc.) The item listing module 346 can receive user selection of the available items displayed on the user interface. Additional details on item listing are provided below in relation to blocks 454 and 456 of FIG. 4B and blocks 502, 504, and 506 of FIG. 5.

In some implementations, the transportation parameters module 348 is configured to obtain transportation parameters for requested items. The transportation parameters can specify a route for the drone to navigate to the pickup (item storage) location and from the pickup location to the drop-off (delivery) location. The transportation parameters can specify the security procedures (e.g., requiring the user to enter an access code to open the secured container) to employ at the pickup and/or drop-off locations. In some cases, the transportation parameters can specify a disinfectant schedule for the item. The disinfectant schedule can be based on a mapping of A) UV illumination intensities and durations to B) the type of the item and the surface materials of the item. The type of item, surface material, and route duration of the drone can be used to determine the intensity and duration needed by the UV lights to reduce the risk of contagion. Additional details on transportation parameters are provided below in relation to block 604 of FIG. 6.

In some implementations, the security module 350 is configured to authenticate a user, recipient or provider, before granting the user access to the item in the secured container on the drone. The user can access the secured container by entering an access code into the locking mechanism on the secured container. The security module 350 can periodically change the access code to protect the item form being accessed by an unauthorized user. In some implementations, the security module 350 can authenticate the user by detecting proximity of the user's registered device with the community item distribution system. In other implementations, the security module 350 can authenticate the user by collecting biometric data of the user, such as fingerprints, facial recognition, or iris scanning. Additional details on container security are provided below in relation to block 508 of FIG. 5 and blocks 604 and 608 of FIG. 6.

Those skilled in the art will appreciate that the components illustrated in FIGS. 1-3 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 4A:
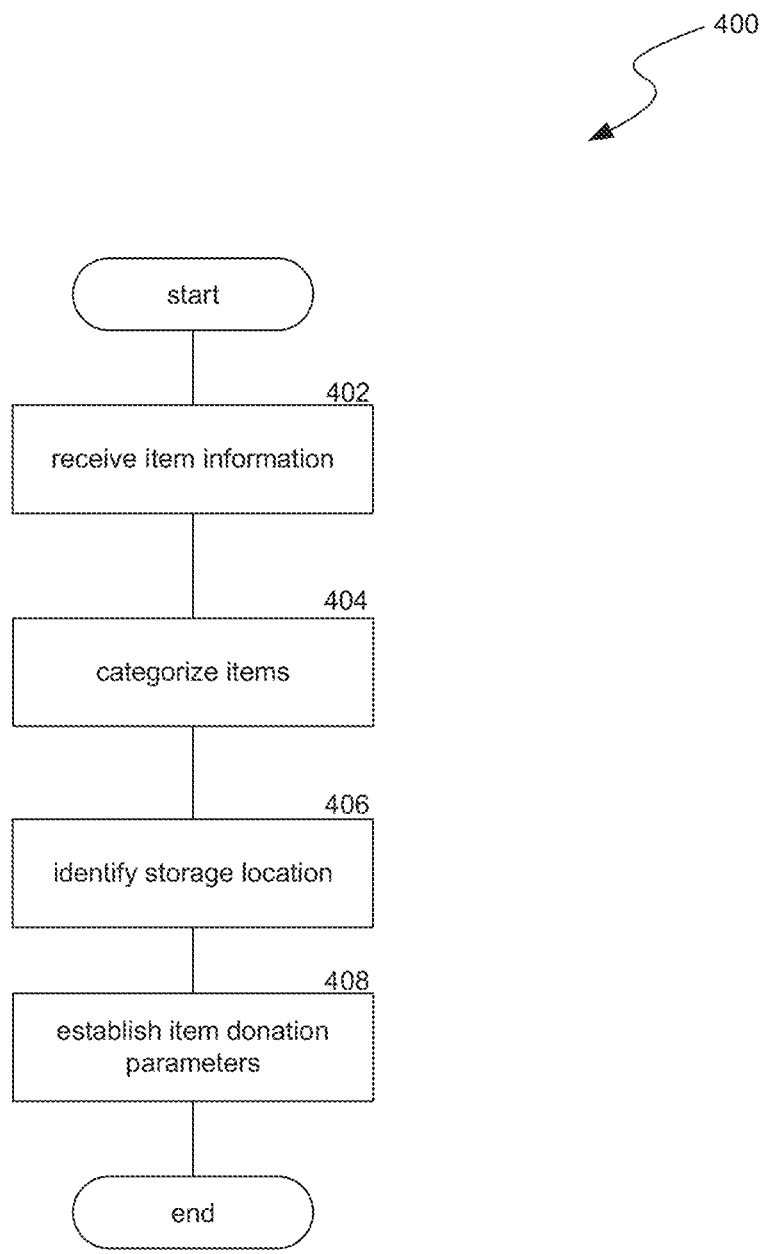
FIG. 4A is a flow diagram illustrating a process used in some implementations of the present technology for receiving community items.

FIG. 4A is a flow diagram illustrating a process 400 used in some implementations for receiving and categorizing community items. In some implementations, parts of process 400 can be initiated by a user applying for an account (or profile), renewing or activating an account for community item distribution, signing into an account or otherwise opening an access point for the community items system (such as an app or website). In various implementations, parts of process 400 can be performed at different times, such as in response to a user activating an account, in response to a user adding items to the community storage, in response to an item expiration, in response to a user requesting items from the community storage, and in response to an event. Process 400 can be a server-side process for a system that coordinates item donation.

At block 402, process 400 can receive item information. The item information can specify item(s) (e.g., food, clothing, tools, cleaning supplies, emergency supplies, household goods, office supplies, electronics, etc.) to be donated to the community. Each item can include characteristics, such as weight, size dimensions, expiration date of food, size of cloths, manufacture date, or item status (e.g., new, used, partially damaged, needs repair, etc.). In some cases, the user can enter the information into the community item distribution system platform (website or application) by uploading pictures of the item (which may be automatically analyzed with machine learning systems to identify item characteristics) or entering characteristics and details of the item. In other cases, the community item distribution system can identify items automatically based on a user's purchase history and upload the item information. For example, a user can periodically donate items to the community by setting up an automated process, such as buying and donating cans of food on a monthly basis to the community or the system can automatically suggest items to a user to donate, where the system can be aware of items the user has based on purchase history (which the system may have access to through user-authorized integrations such as with a payment platform or retailer). In other cases, the community item distribution system can identify items and characteristics from information the user has provided. For example, the community item distribution system can select items the user can donate based on the user providing the system access to information, such as from object recognition of items in images (or videos) the user provided of her pantry/fridge/closet. The community item distribution system can identify item information from purchase history/records (e.g., credit card statements) the user has granted the system access to, or by the user scanning bar/QR codes of items and uploading the information associated with the code. In some implementations, the user can deliver the donated items to a centralized storage facility where the items are documented, or the items can remain with the user until a recipient requests the item.

At block 404, process 400 can categorizing the items according to item type categories (e.g., food (perishable, canned, etc.), tools, sporting goods, clothing, cleaning supplies, electronics, location of item (area codes, threshold distance from the recipient's location), etc. The categorization of the items can be based on A) user provided categories when the donating the item, B) by using a set of categories pre-defined for known item types, and/or C) by using a machine learning (ML) model trained to receive item images and/or tags and classify the item. Item categorization may be performed by a machine learning model trained to identify items and item categories. Such a machine learning model can be trained using previously identified items in item categories paired with images of those items. For example, the user may buy cans of food and upload the images of the cans along with receipt data or description of the canned food, and the machine learning model can identify cans of food in future uploaded images based on the previously identified cans of food.

A "machine learning model" or "model" as used herein, refers to a construct that is trained using training data to make predictions or provide probabilities for new data items, whether or not the new data items were included in the training data. For example, training data for supervised learning can include positive and negative items with various parameters and an assigned classification. A new data item can have parameters that a model can use to assign a classification to the new data item. As another example, a model can be a probability distribution resulting from the analysis of training data, such as a likelihood of an event occurring in a given timeframe based on an analysis of a large corpus of events with corresponding times. Examples of models include: neural networks, support vector machines, decision trees, Parzen windows, Bayes, clustering, reinforcement learning, probability distributions, decision trees, decision tree forests, and others. Models can be configured for various situations, data types, sources, and output formats.

In some implementations, a community item distribution model can be a neural network with multiple input nodes that receive item data. The input nodes can correspond to functions that receive the input and produce results. These results can be provided to one or more levels of intermediate nodes that each produce further results based on a combination of lower level node results. A weighting factor can be applied to the output of each node before the result is passed to the next layer node. At a final layer, ("the output layer,") one or more nodes can produce a value classifying the input that, once the model is trained, can be used as an item categorization. In some implementations, neural networks, known as deep neural networks, can have multiple layers of intermediate nodes with different configurations, can be a combination of models that receive different parts of the input and/or input from other parts of the deep neural network, or are convolutions-partially using output from previous iterations of applying the model as further input to produce results for the current input.

The community item distribution model can be trained with supervised learning, where the training data includes the positive and negative training items as product data for items as a desired output paired with input such as an item image. In training, output from the model can be compared to the desired output for that item and, based on the comparison, the model can be modified, such as by changing weights between nodes of the neural network or parameters of the functions used at each node in the neural network (e.g., applying a loss function). After applying each of the item category pairings in the training data and modifying the model in this manner, the model can be trained to evaluate new item images to produce item categories.

In some cases, the categories can include sub-categories which organize the types of items by weight, size dimensions, age of the item, expiration date, purchase date, value of the item, or multitude of the item in storage. In some implementations, process 400 can allocate a point value or score to a donated item according to a predefined mapping based on the item type. For example, the score can be based on the cost of the item or a formula that defines a point value based on a quantity for the item (e.g., weight, volume, calorie count, nutritional value, etc.) and item category/sub-category. In an example, if an item is donated frequently and in great quantity (such as canned soup) process 400 can assign a lower score to the item than a rare item (such as jewelry). In another example, points can be allocated to a food item according to its caloric count and category: such as 500 calories of a protein item being allocated 50 points while 500 calories of a sugar-heavy items such as barbeque sauce being allocated 25 points. In some implementations, the donating user can receive a percentage score/points assigned to the user's account/profile for each donated item. The such score or points can be used as "currency" for other items in the system. For example, a user receives points for donating items and spends points when requesting items. In some cases, the score associated with a user's account can determine the amount that a user can request from the community. As an example, each time a recipient user requests an item from the community, a number of points is deducted from the user account. In some implementations, a user can be allocated a certain number of points per time period (e.g., day or week), allowing them to access items in the system without having to donate themselves. For example, a family of four can be allocated 5000 points per week, allowing them to select items that would be most beneficial to them, while limiting people from simply taking as much as they want from the community. Thus, before an item is delivered to a recipient user, process 400 may verify if the recipient user has sufficient points to request the item.

At block 406, process 400 can identify a storage location for the donated item(s). Process 400 can track and document the location for the items. In an example, if the user drops off the items at a centralized storage facility for community item distribution, process 400 can identify the location of the facility. In another example, if the items are stored at the donator's home, property, or place of employment, process 400 can identify the location the donator has selected. In some cases, the type of item can determine the storage location. In an example, perishable items, such as food, must be stored at a donator location, but nonperishable items, such as clothing, can be stored at any location. In another example, the size dimensions or weight can determine the storage location, such as an item above a threshold weight or size must be brought to a storage facility, as they are not eligible for drone pickup. In some implementations, the storage location is a vehicle (e.g., a drone, truck, van, etc.) which picks up, stores, and delivers items. The vehicle can have an internal item management system which monitors the expiration dates of the items in the vehicle.

At block 408, process 400 can establish item donation parameters for the items. The donation parameters can specify donation specifics such as where the item can be provided (e.g., delivered to or, if stored at a distribution facility, where it can be picked-up from) or when it can be provided (e.g., prior to an expiration date, or a time the donating user specifies that they will be available to load the item into a drone). The donation parameters of the items can be based on the categorizations of the items, the expiration date, weight, size dimensions, or storage location of the item. For example, various ranges of values in these categories can be mapped to corresponding donation parameters. In some cases, process 400 can monitor the viability of the items and remove expired items. For example, if analysis shows the item is expired or about to expire within a threshold of time (e.g., any time threshold, such as minutes, hours, days or months), then the item is automatically removed from being selectable by recipients in the community item distribution system.

Figure 4B:
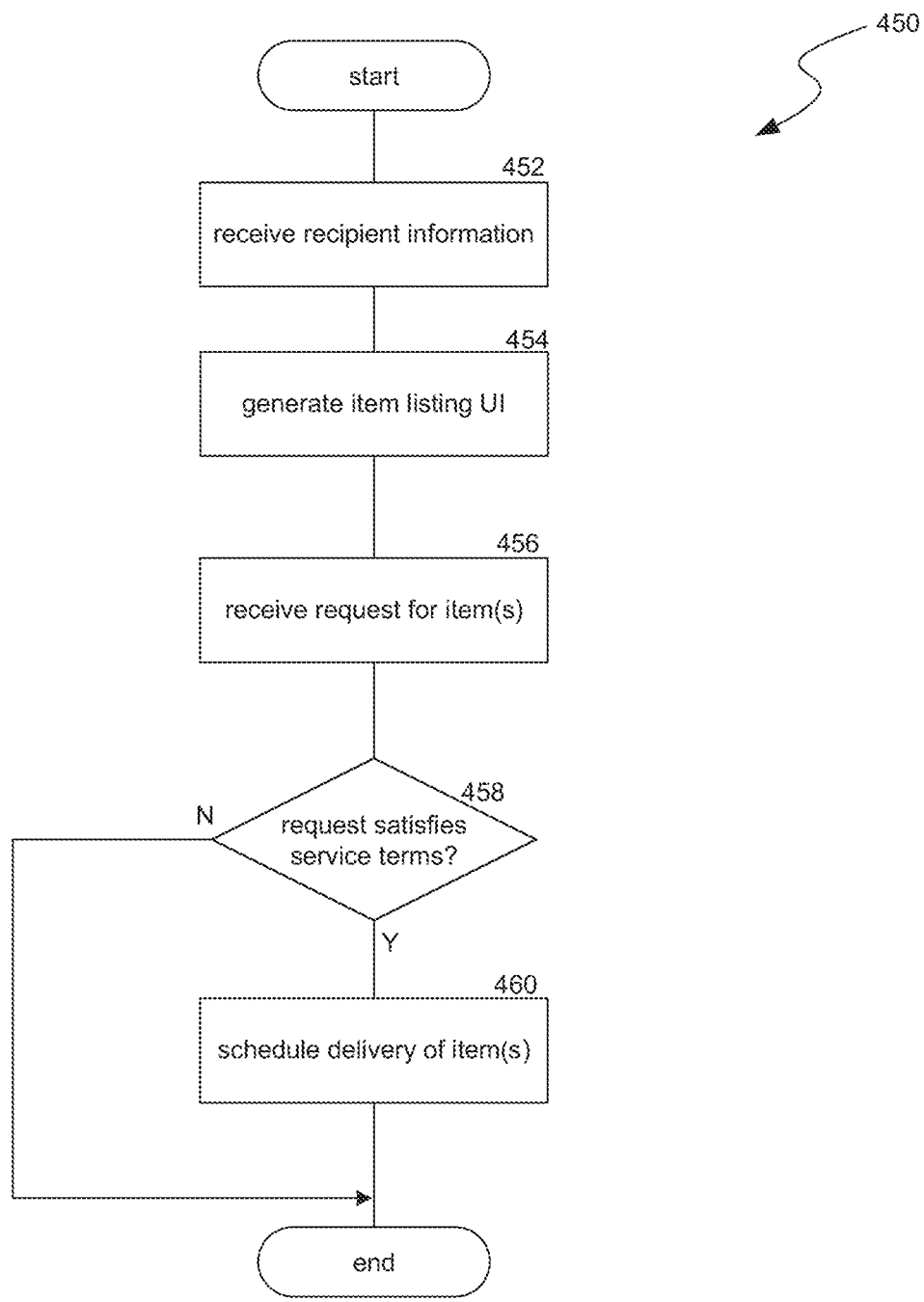
FIG. 4B is a flow diagram illustrating a process used in some implementations of the present technology for distributing community items.

FIG. 4B is a flow diagram illustrating a process 450 used in some implementations for receiving recipient information and scheduling delivery of community items. In some implementations, parts of process 400 can be initiated by a user applying for an account (or profile), renewing or activating an account for community item distribution, signing into an account or otherwise opening an access point for the community items system (such as an app or website). Process 450 can be a server-side process for a system that coordinates item delivery.

When creating an account in the community item distribution system, the user can enter information regarding item pickup locations, delivery locations, home address, device information so the system can retrieve the device's current location, or security information such as passwords, access codes, typing cadence, facial recognition, fingerprints, voice recognition, or iris recognition. At block 452, process 450 can receive recipient information specifying a delivery location (e.g., an address, a location associated with a device of a recipient user, etc.) Process 450 can receive the recipient information, such as the recipient's delivery location, from the user account or by retrieving the location of the user device. Process 450 can select available items that the user can request based on determining items with donation parameters that match the delivery location or that the recipient user is qualified to request. In some cases, the delivery location must be below a threshold distance (0.5 miles, 1 mile, etc.) from the storage location. This can ensure timely and cost-effective delivery. In some implementations, after a recipient selects an item, a version of that item closest to the delivery location can be selected for delivery. Process 450 can also select available items based on the identity of the recipient user. In an example, certain items may be reserved for homeless users, family members of people deployed in the military, users eligible for state assistance, household income levels, users affected by a natural disaster, or users in rehabilitation or recovery facilities. In another example, process 450 can select available items based on the amount of points or score (as described at block 404 of FIG. 4A) of the recipient user, such as the only selecting items that the user has sufficient points to request.

At block 454, process 450 can generate an item listing user interface (UI) for the selected available items. The listed items can be items that the recipient is eligible to receive. Process 450 can list items that the user can go pick up or list items that the user can have delivered. In some cases, process 450 can list items that the user has sufficient points to request. In other cases, process 450 can list items and the required points needed by the user to request the items. Process 450 can list items that are within a threshold distance (e.g., any threshold distance, such as 0.1 miles, 0.5 miles, 1 mile, etc.) of the recipient. The UI can have controls the recipient can use such as filters or category selectors, such as clothing sizes, food preferences, distance to pickup or drop off, brands of tools or equipment, clean supplies, emergency supplies, or brands of electronics. In some implementations, process 450 lists the items that are in a storage vehicle within a threshold distance of user.

At block 456, process 450 can receive a request for one or more items. The user can submit the request by selecting items in the UI. In some cases, the recipient may select a category sub-type and process 450 can select the item in that category to deliver. For example, the user can select, in the category of food, the sub-type of bread and process 450 can select hamburger rolls from the variety of items (e.g., hamburger rolls, hot dog rolls, baguette, bagels, etc.) in the sub type of bread that the requesting user is eligible to receive (e.g., that is within a threshold distance and/or that the user has sufficient points to receive). Process 450 can receive the request and locate and select the item(s) nearest the delivery location (e.g., recipient's location or a storage location, such as a locker). If the request is food, process 450 can locate items nearest to expiration, so those items do not get disposed of before expiring.

At block 458, process 450 can determine if the request satisfies service terms for distribution of community items. In some cases, the service terms can be based on the recipient, such as restrictions of the amount of items per user per time threshold (e.g., any time threshold, hours, days, or months), whether the recipient has sufficient points in her account of the requested item, qualifying events (loss of job, natural disaster in user's area, eligible for state assistance, deployed family member in the military, household income levels), items reserved for people in rehab or recovery centers. In other cases, the requested item can be reserved for emergencies (e.g., pandemics, fires, floods, etc.) and the user must provide verification of her need for the emergency supplies. If the request does not satisfy the service terms, process 450 can cancel the request.

At block 460, process 450 can schedule a drone, which may have a secured and/or disinfecting container, to obtain the requested item(s) from the storage location and deliver the item(s) to the delivery location. Process 450 can select the size and type (flying or land based) of drone based on the weight of the item, size dimensions of the item, storage location, delivery location, and/or distance of the route to the item pickup location and the route to the delivery location to drop off the item. Process 450 can coordinate with the user at the storage location and the recipient user at the delivery location for times of pick up and drop off. Process 450 can provide notifications on the UI about the pickup and delivery status of the items. In some cases, the recipient user and/or the user at the storage location can be provided access codes for the secured container on the drone. In some implementations, when there is no drone, the provider user can deliver the item to locker or other central facility, for the recipient user to retrieve. Process 450 can send the recipient and the provider the location of the locker or facility, locker number, and code to access the locker.

Figure 5:
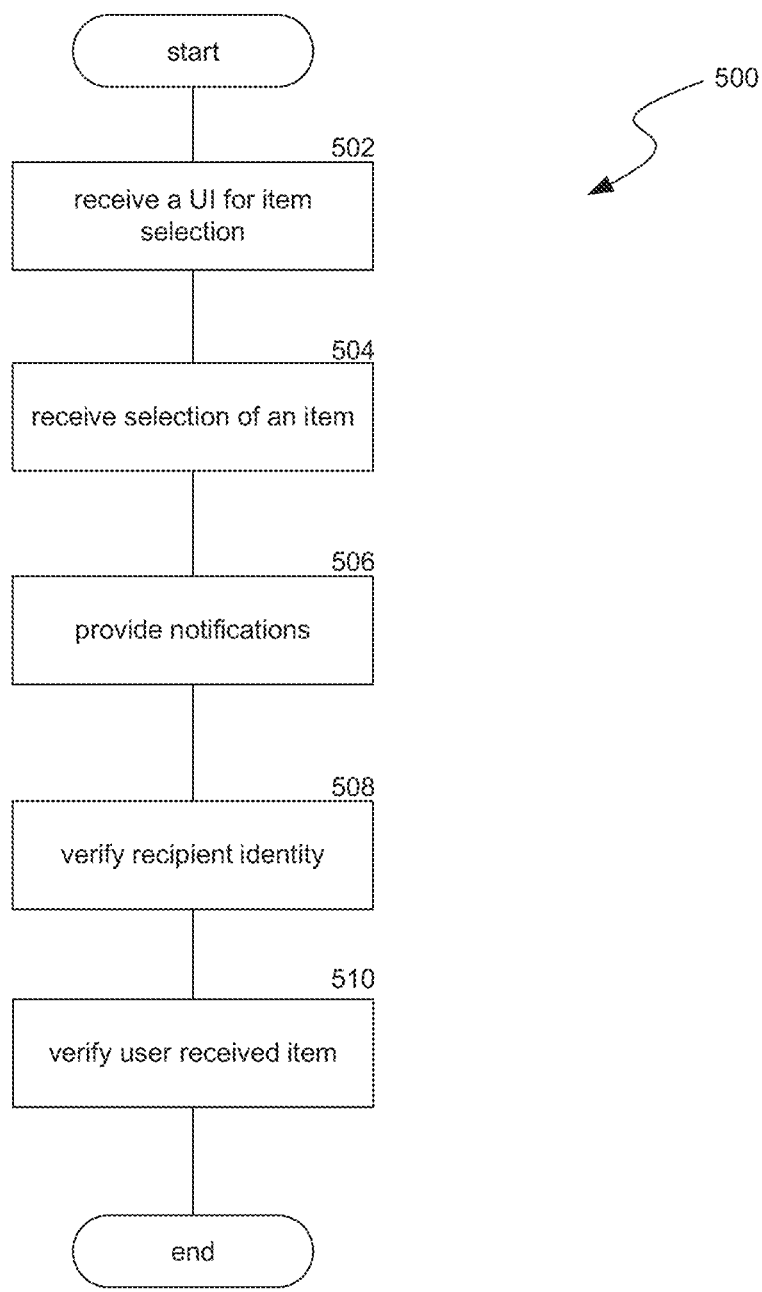
FIG. 5 is a flow diagram illustrating a process used in some implementations for receiving recipient item selections and coordinating delivery of the selected items.

FIG. 5 is a flow diagram illustrating a process 500 used in some implementations for receiving recipient item selections and coordinating delivery of the selected items. In some implementations, parts of process 400 can be initiated by a user applying for an account (or profile), renewing or activating an account for community item distribution, signing into an account or otherwise opening an access point for the community items system (such as an app or website). Process 500 can be a client-side process for a system that coordinates item delivery, as a companion process to process 450.

At block 502, process 500 can receive a UI (generated in block 454 of FIG. 4B) for item selection on the recipient user's device. At block 504, process 500 can receive a selection, from a recipient user, of an item on the UI. In some implementations, the recipient can filter and/or search for products, e.g., by category, sub-category, or item type. The UI can be configured to allow the recipient to select items, mark items as "favorites", save items for later, save item searches, reserve items, add items to a cart, and checkout the items. Checking out the items can initiate the delivery request process as discussed at block 460 of FIG. 4B. The recipient can select a preference in the UI of the type of delivery, such as delivery by drone or pickup at a locker location. The recipient can select a window of time to have the item delivered or to pick up the item. In some cases, process 500 only displays items to the recipient based on the recipients account status. For example, some items are restricted by the number of items per user, per day, calorie amounts of the items, qualifying events (loss of job, natural disaster in user's area, eligible for state assistance, deployed family member, household income levels), or users in rehabilitation or recovery centers.

At block 506, process 500 can provide notifications on the UI to the recipient about the delivery status of the selected item. The recipient can receive location information regarding where the drone will deliver the item. The delivery location can be determined based on the GPS location of the user's device. In some cases, the user can select in the UI a delivery location. For example, the user can select a delivery location from a list of available delivery locations, or the user can enter the address of a particular delivery location. The notifications can include the item is on its way, the drone is scheduled to arrive in an amount of time (e.g., 10 min, 20 min, etc.), the locker number, locker access code, access code to the secured container on the drone, address of distribution center where item is stored, verification receipt of the requested item, window of time to retrieve the item at the locker location or secured container on the drone, window of time that the access code is active (e.g., the access code changes periodically), the amount of points the user has in her account, the delivery location, description of the drone, image of the drone, etc.

At block 508, process 500 can verify the identity (authenticate the user) of the recipient at the delivery location. Process 500 can verify the recipient's identity based on the recipient entering the access code on a key pad, scanning a code on the recipient's device, recipient's biometric data (e.g., typing cadence, facial recognition, fingerprints, voice recognition, or iris recognition). In some cases, the process 500 can verify the identity of the recipient by detecting the proximity (e.g., using near field communication detection) of the recipient's device used to request the item. In other cases, process 500 may not verify the identity of the recipient and the drone can deliver the item to the delivery location without identity verification.

At block 510, process 500 can verify the recipient received the item by determining if the user accessed the locker or secured container on the drone. If the recipient does not access the locker or secured container within a time threshold, process 500 can send the recipient an alert on the UI. In some cases, if the item is not retrieved by the recipient, the drone can return the item to the storage location. Additional details on drone delivery procedures are provided in FIG. 6.

Figure 6:
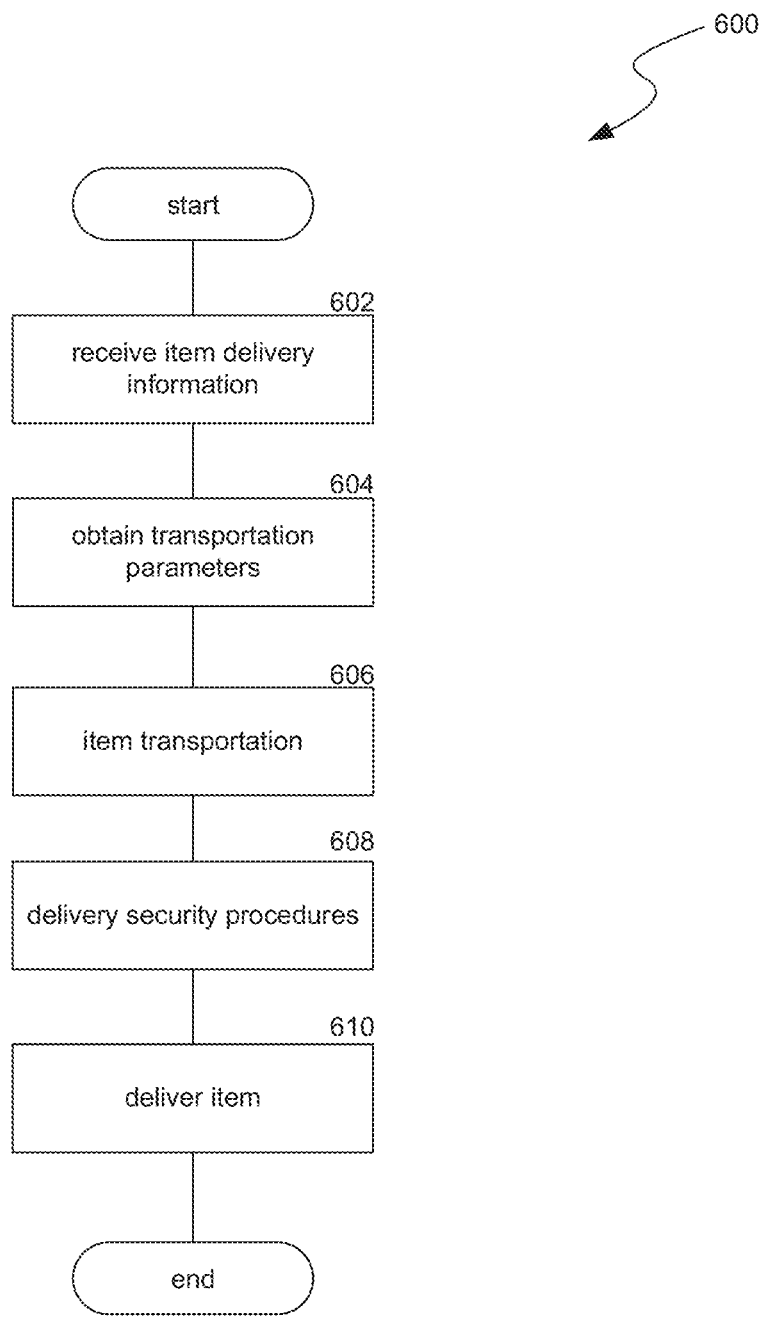
FIG. 6 is a flow diagram illustrating a process used in some implementations of the present technology for a drone disinfecting and delivering community items.

FIG. 6 is a flow diagram illustrating a process 600 used in some implementations for delivering community items with a drone. In some implementations, parts of process 600 can be initiated by a user requesting an item or by the community item distribution system scheduling a pick up and/or delivery of an item. In some implementations, process 600 is triggered by the completion of block 460 in FIG. 4B.

Figure 7A:
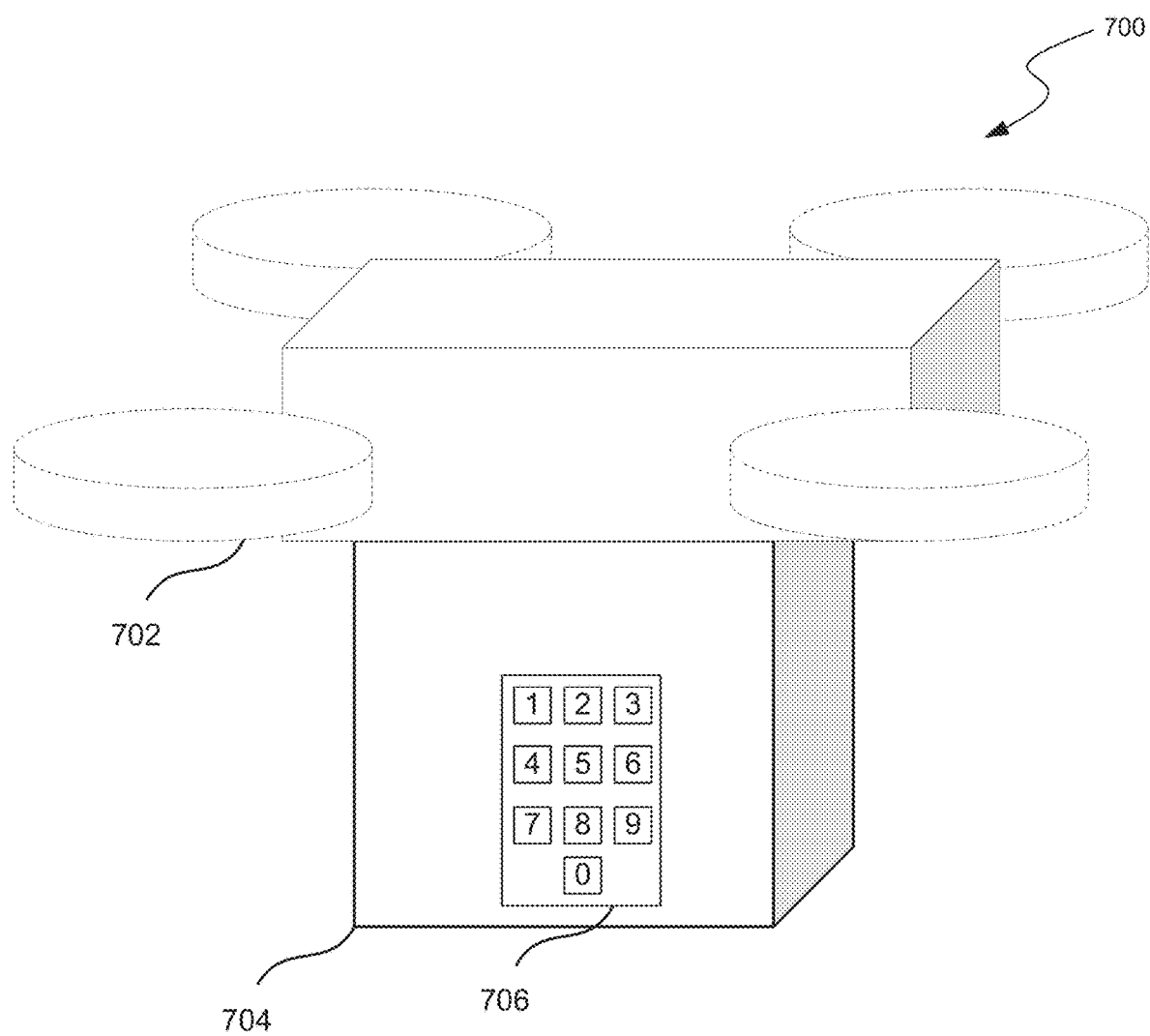
FIG. 7A is a conceptual diagram illustrating an example of a flying drone with a secured container.
Figure 7B:
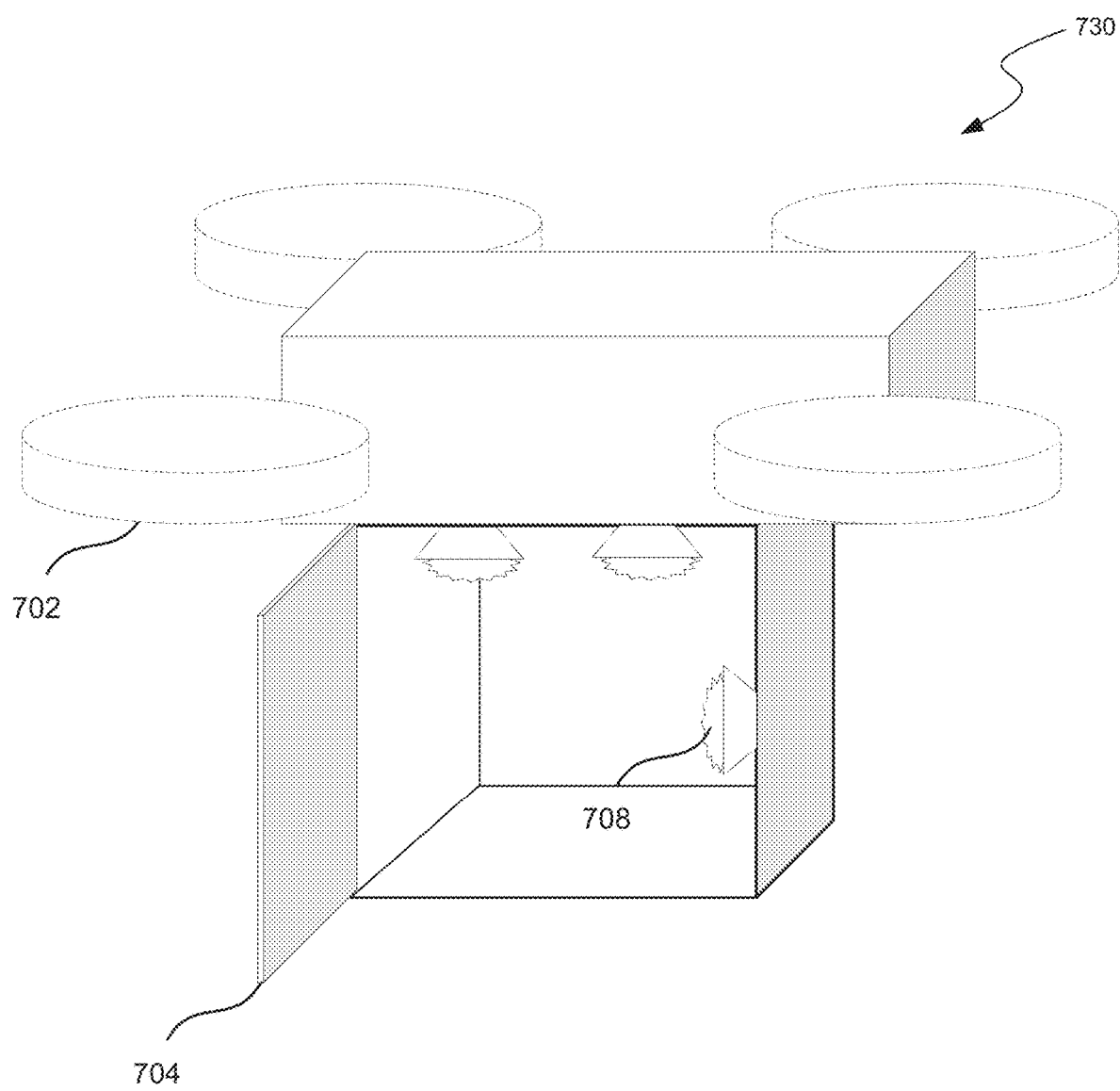
FIG. 7B is a conceptual diagram illustrating an example of a flying drone with a secured container with a disinfectant system.
Figure 7C:
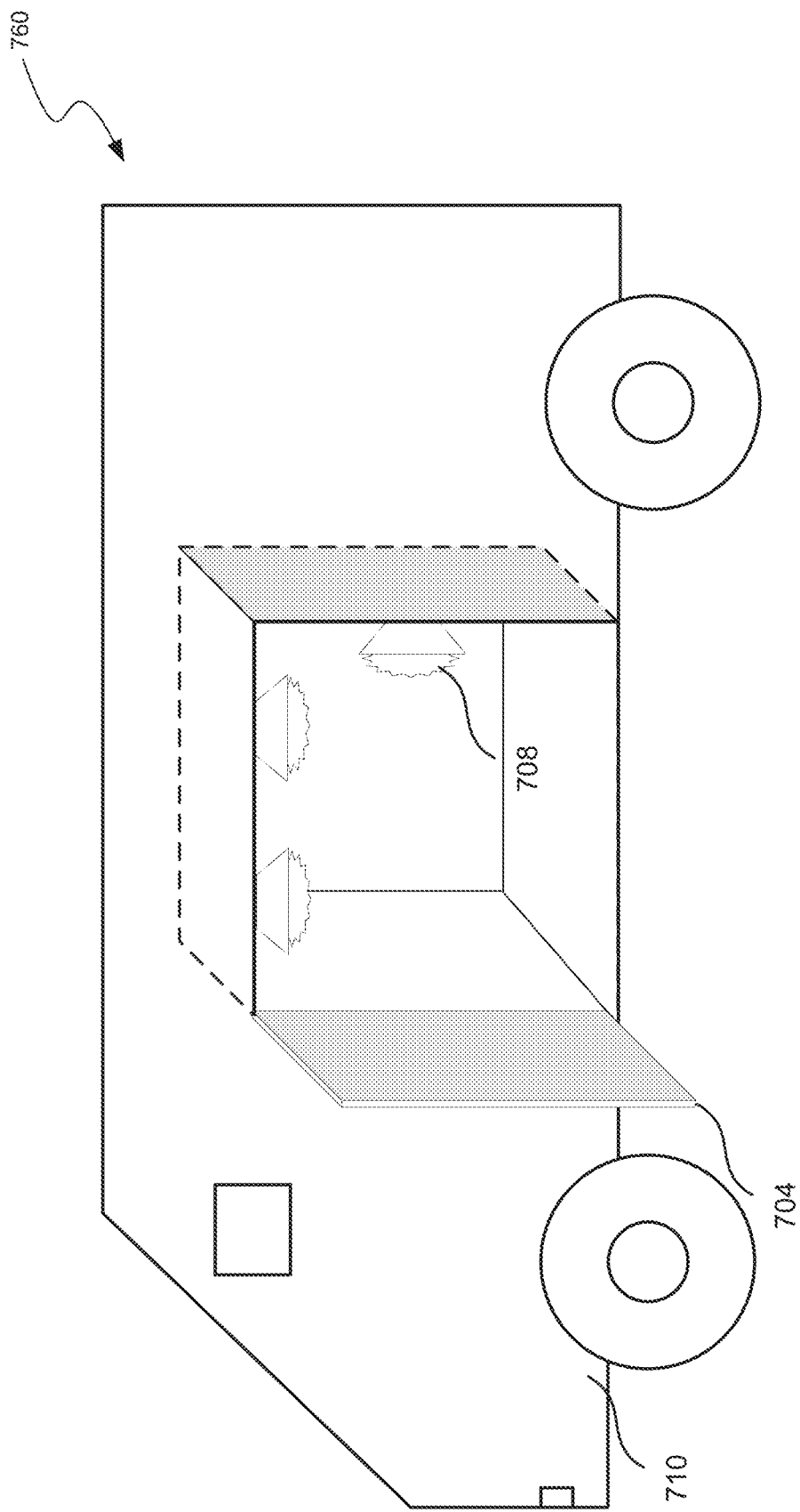
FIG. 7C is a conceptual diagram illustrating an example of a land-based drone with a secured container with a disinfectant system.

In some implementations, a community item distribution system can utilize a drone (flying or land-based) to pick up and deliver items between locations. The drone can be equipped with a secured container (locker) with a locking mechanism. FIG. 7A illustrates example 700 of a flying drone 702, with a secured container 704 with a locking mechanism 706. In some cases, the secured container can contain one or more ultraviolet (UV) disinfecting lights, ozone systems, chemical (e.g., alcohol vapor) sprayers, or other mechanism to disinfect the items stored in the secured container. Disinfecting items can increase the safety of the community by stopping the spread of bacteria, viruses, germs, or parasites. FIG. 7B illustrates example 730 of a flying drone 702, with a secured container 704 with UV disinfecting lights 708 inside the secured container 704. FIG. 7C illustrates example 760 of a land-based drone 710, with a secured container 704 with UV disinfecting lights 708 inside the secured container 704. In some implementations, disinfecting lights 708 can be replaced with other disinfectant delivery systems such as for ozone or alcohol.

At block 602, process 600 can receive item delivery information for a requested item(s). Process 600 can receive the delivery information from the community item distribution system as a result of an item request order being processed. The delivery information can include pickup (storage) and drop-off (delivery) location information, size dimensions and weight of the item, description of the item, provider user identity information (e.g., access code, facial recognition, etc.), and/or recipient user identity information. In some implementations, process 600 can select the type of drone for the delivery based on the route distance, pickup location, delivery location, size dimensions, and/or weight of the item. For example, a land-based drone may be used to transport large or heavy objects, such as a wardrobe, while a flying drone may be used to transport smaller or lighter objects, such as a loaf of bread.

At block 604, process 600 can obtain transportation parameters for the requested item(s). The transportation parameters can specify a route from the drone's location to the pickup location, and a route from the pickup location to the drop off location. The transportation parameters can specify altitude and speed of the drone for each route. In some implementations, the transportation parameters can specify security procedures for the drone to employ at the pickup and drop-off locations. The security procedures can include requiring the user (recipient and/or provider) to enter an access code (e.g., QR code, password, key code, scan code, barcode, etc.) to unlock the locking mechanism and access the secured container. In some cases, the security procedures can require the users at the pickup and drop-off locations to provide biometric data (e.g., fingerprint, facial recognition, iris scanning, etc.) to verify their identities. In some implementations, the access code at the pickup location is the same as the access code at the drop-off location. In other implementations, the access code is different at the pickup and drop-off locations. The access code can be user generated or user specific. For example, the provider user and the recipient user can each have their own access codes. In some cases, the community item distribution system generates the access codes and sends the access codes to the item provider and recipient users.

In some implementations, the transportation parameters can specify a disinfectant schedule for the requested item(s). The disinfectant schedule can include UV illumination intensities and durations by the UV lamps, amount of chemical (e.g., alcohol, antibacterial or antiviral agents, or ozone) to emit, etc. In some cases, a drone can include multiple disinfecting systems (e.g., UV light and alcohol vapor spray) and the disinfecting schedule can specify which or multiple to use, e.g., based on types of items in the secured container and a determined level of disinfecting needed. In some cases, the UV illumination intensities and durations, amounts of chemical, or other disinfecting parameters can be based on the type of item and/or the surface materials of the item. For example, smooth surfaces, such as glass or plastic, disinfect faster that rough surfaces, such as cardboard. In some cases, the disinfectant schedule can be based on a mapping of A) UV illumination intensities and durations to B) the type assigned to the item and the surface materials of the item. For example, food would have a different UV intensity and duration to kill bacteria than clothes. In some cases, the disinfectant schedule is based on the location of the delivery. For example, if the delivery is occurring from or to a country or city suffering from a pandemic, the disinfectant schedule may be varied from a disinfectant schedule of a delivery to or from a city or country without such health concerns. In other cases, the disinfectant schedule is based on the time of year. For example, if the delivery is occurring during a flu season, the disinfectant schedule may be varied from a disinfectant schedule during a non-flu season.

The disinfectant schedule can be predetermined based on the category, type, and characteristics of the item that the community item distribution system has documented for the item. In some cases, the disinfectant schedule is based on the duration of the drone route. Scientific studies have shown that high intensities for a short period of time and low intensities for a long period of time are fundamentally equal in lethal action on bacteria. In an example, when the drone travel route is a long duration (e.g., 20 minutes), the UV intensity can be decreased (to save drone power) based on the long duration of the route. In another example, when the drone travel route is a short duration (e.g., 5 minutes), the UV intensity can be increased to kill the bacteria during the short route duration.

In some implementations, process 600 automatically identifies the one or more surface materials of the items by capturing images of the item and applying a machine learning model trained to produce surface material determinations (trained using training items that pair item images to surface type tags). Process 600 can capture images of the item using cameras directed toward the interior of the secured container.

In some cases, the mapping used to determine the disinfectant schedule for the item(s) is based on a machine learning model trained to determine disinfectant schedules for items. The machine learning model can be trained based on previously observed effectiveness rates for UV disinfecting lights, at various intensities, for various durations, and for items of various surface types. In some implementations, process 600 can disinfect the items with an ozone generator in addition to or in place of the UV lights. The disinfectant schedule of the ozone generator can be based on the surface of the item, the type of item, and the duration of the drone route.

In some implementations, process 600 can perform tests to determine whether the drone has enough stored energy to perform the disinfectant schedule at the UV illumination intensity and required duration. Process 600 can select the drone based on the energy level needed to power the disinfectant schedule for the item. In some cases, process 600 can perform tests to verify that all the UV lamps are operating at above a threshold of intensity. When deficient lamps are detected (e.g., operating below the threshold of intensity), process 600 can schedule the drone for maintenance and remove the drone from the list of available drones until the lamps are replaced.

At block 606, process 600 can perform the item transportation. The drone can travel the route to the pickup location (e.g., rooftop, patio, or designated drone pick up location) where the item is stored and unlock locking mechanism on the secured container upon arrival at the pickup location. In various implementations, the drone can use existing autonomous navigation techniques to traverse the routes to the pickup and drop-off locations. For example, the drone can use various mapping systems, sensor, and camera systems to orient itself, identify and navigate obstacles, and reach objectives.

Upon arrival at the pickup location, the provider user can place the item in the open secured container. In some cases, process 600 verifies the identity of the provider user by requiring the user enter the access code to unlock the secured container before placing the item inside the container. Upon receiving the item, the drone can perform a weight test to determine if the drone can safely lift/transport the item to the delivery location without damaging the drone. In some cases, if the item weight is more than the transportation capacity of the drone or if the item does not fit in the secured container, process 600 can schedule another drone able to support the weight or size of the item to perform the delivery.

Once the item is locked in the secured container, the drone can travel the route form the pickup location to the delivery location while engaging the one or more UV disinfecting lights according to the disinfectant schedule. In some cases, the transportation parameters can indicate the item is for an emergency event, in which case the drone may travel the route at an accelerated rate compared to the rate of travel for a non-emergency event. In some implementations, based on the determined weight and/or dimensions of the item, the drone may travel to an intermediate location and transfer the item to a second drone to transport the item to the delivery location. In other implementations, if process 600 detects a failure in the drone, the drone may cease travel or travel to an intermediate location and transfer the item to a second drone to transport the item to the delivery location.

Process 600 can determine the disinfectant schedule is not complete prior to arrival at the delivery location. In some cases, process 600 can instruct the drone to hover or remain stationary at a location until the disinfectant schedule is determined to be complete. In other cases, process 600 can delay unlocking the locking mechanism of the secured container until the disinfectant schedule is complete. In some implementations, the drone performs the disinfectant schedule upon arrival at the delivery location.

At block 608, process 600 can execute security procedures upon arrival at the delivery location. In some implementations, process 600 can perform an authentication of the recipient at the delivery location by requiring the recipient to enter the access code to open the locking mechanism on the secured container. In some cases, process 600 can require the user to provide biometric data (e.g., facial recognition, iris scanning, etc.) to unlock the secured container. In yet other cases, process 600 can verify the identity of the recipient by detecting the proximity of the recipient's device. Additional details regarding verifying the recipient's identity is located at block 508 of FIG. 5.

At block 610, process 600 can unlock the locking mechanism of the secured container and permit the recipient to retrieve the item, once the security procedures are executed. The drone can mark the delivery location for the recipient with a light projection (e.g., a shape) on the ground. In some cases, the drone can play a prerecorded message to give the recipient instructions for accessing the secured container.

In some implementations, the drone can deliver the item to a locker facility. An employee at the facility can unlock the secured container by entering the access code and place the item in a locker or storage unit for the recipient user to retrieve. In other implementations, the delivery from the drone to the locker can be an automated process in which the drone delivers the item to the locker without human interaction. For example, as the drone arrives at the delivery location, it can communicate with a locker, so the locker door and the secured container door open at similar times, and the drone delivers the item into the locker. Once the item is in the locker, the locker door can securely close until the recipient retrieves the item with the delivery security procedures.

The distribution systems disclosed herein can be used to distribute items within and/or between community item distribution systems, food delivery systems (e.g., restaurant food delivery systems, grocery delivery systems, etc.), or other distribution systems. For example, pick-up locations can be food donation centers, restaurants, grocery stores, or the like. The drones can select and perform disinfecting routines based on, for example, one or more characteristics of the items (e.g., temperature, flavor, packaging, etc.), environmental conditions (e.g., humidity, ambient temperature, etc.), whether the drone has multiple containers for multiple drop-offs, etc. The number, configurations, and capabilities of the drones can be selected based on, for example, items to be carried and scheduling.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Reference in this specification to "implementations" (e.g. "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle specified number of items, or that an item under comparison has a value within a middle specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

I claim:

1. A method for delivering community items via a drone equipped with a secured container, the drone comprising a locking mechanism and one or more ultraviolet (UV) disinfecting lights, the method comprising:
receiving delivery information for one or more items;
obtaining transportation parameters, for the one or more items, specifying:
a first route to a pickup location;
a second route from the pickup location to a drop-off location;
security procedures to employ at the drop-off location; and
a disinfectant schedule for the one or more items specifying UV illumination intensities and/or durations, wherein:
the disinfectant schedule specifies how the illumination intensities and/or durations are set based on a determined category of the one or more items, and/or
the disinfectant schedule specifies how the illumination intensities and/or durations are set based on a determined duration for the second route;
using the first route to travel to the pickup location and unlocking a locking mechanism of the secured container in response to arriving at the pickup location, wherein the secured container receives the one or more items at the pickup location;
using the second route to transport the one or more items to the drop-off location while disinfecting the one or more items by engaging the one or more UV disinfecting lights according to the disinfectant schedule with the illumination intensities and/or durations for the determined category of the one or more items and/or determined duration for the second route; and
upon arriving at the drop-off location, executing the security procedures including:
performing an authentication; and
in response to the authenticating, unlocking the locking mechanism of the secured container.

2. The method of claim 1, wherein the disinfectant schedule is further based on automatically identifying one or more surface materials, of the one or more items, by:
capturing one or more images of the one or more items, using one or more cameras directed toward the interior of the secured container; and
applying a machine learning model trained to produce surface material determinations.

3. The method of claim 1, further comprising:
determining the disinfectant schedule is not complete prior to arriving at the delivery location; and
delaying unlocking the locking mechanism of the secured container until the disinfectant schedule is complete.

4. The method of claim 1,
wherein obtaining the transportation parameters comprises determining the one or more items are for an emergency event; and
wherein the drone uses the second route at a rate determined based on the emergency event.

5. The method of claim 1,
wherein obtaining the transportation parameters comprises determining a weight and/or dimensions of the one or more items; and
wherein, based on the determined weight and/or dimensions, the second route is a route to an intermediate location at which the one or more items are transferred to a second drone to transport the one or more items to a delivery location.

6. The method of claim 1, wherein the drone is a flying drone and wherein the second route includes a flight route and flight time of the drone.

7. The method of claim 1, wherein the disinfectant schedule is determined using a machine learning model trained to determine disinfectant schedules for items, wherein the machine learning model was trained based on previously observed effectiveness rates for UV disinfecting lights, at various intensities, for various durations, and for items of various surface categories.

8. A computing system for delivering items via a drone equipped with a secured container, the drone comprising one or more disinfecting systems, the computing system comprising:
one or more processors; and
one or more memories storing instructions that, when executed by the one or more processor, cause the computing system to perform a process comprising:
receiving delivery information for one or more items;
obtaining transportation parameters, for the one or more items, specifying:
a first route to a pickup location;
a second route from the pickup location to a drop-off location; and
a disinfectant schedule, wherein:
the disinfectant schedule specifies how illumination intensities and/or durations are set based on a determined category of the one or more items, and/or
the disinfectant schedule specifies how the illumination intensities and/or durations are set based on a determined duration for the second route;
using the first route to travel to the pickup location, wherein the secured container receives the one or more items at the pickup location; and
using the second route to transport the one or more items to the drop-off location while disinfecting the one or more items by engaging the one or more disinfecting systems according to the disinfectant schedule with the illumination intensities and/or durations for the determined category of the one or more items and/or determined duration for the second route.

9. The computing system of claim 8, wherein the engaging the one or more disinfecting systems is performed according to the disinfectant schedule that is further based on automatically identifying one or more surface materials, of the one or more items, by:
capturing one or more images of the one or more items, using one or more cameras directed toward the interior of the secured container; and
applying a machine learning model trained to produce surface material determinations.

10. The computing system of claim 8, wherein the engaging the one or more disinfecting systems is performed according to the disinfectant schedule and wherein the process further comprises:
determining the disinfectant schedule is not complete prior to arriving at the drop-off location; and
delaying unlocking a locking mechanism of the secured container until the disinfectant schedule is complete.

11. The computing system of claim 8,
wherein the disinfecting systems include one or more chemical dispensing systems; and
wherein the disinfectant schedule is further based on a mapping that correlates A) amounts of chemical to dispense to B) the one or more categories assigned to the one or more items and/or the one or more surface materials of the one or more items.

12. The computing system of claim 11, wherein the mapping used to determine the disinfectant schedule for the one or more items is based on a machine learning model trained to determine disinfectant schedules for items, wherein the machine learning model was trained based on previously observed effectiveness rates for chemical disinfecting procedures on items of various surface categories.

13. The computing system of claim 8,
wherein the drop-off location is an intermediate location; and
wherein the second route is a route to the intermediate delivery location at which the one or more items are transferred to a second drone to transport the one or more items to a delivery location.

14. The computing system of claim 8, wherein the drone is a flying drone and wherein the second route includes a flight route and flight time of the drone.

15. A non-transitory machine-readable storage medium having machine executable instructions stored thereon that, when executed by one or more processors, direct the one or more processors to perform a process for delivering items via a drone equipped with a secured container, the drone comprising one or more disinfecting systems, the process comprising:
receiving delivery information for one or more items;
obtaining transportation parameters, for the one or more items, specifying:
a route from a pickup location to a drop-off location; and
a disinfectant schedule, wherein:
the disinfectant schedule specifies how illumination intensities and/or durations are set based on a determined category of the one or more items, and/or
the disinfectant schedule specifies how the illumination intensities and/or durations are set based on a determined duration for the second route;
causing the drone to receive, in the secured container, the one or more items at the pickup location;
using the route to transport the one or more items to the drop-off location while disinfecting the one or more items by engaging the one or more disinfecting systems according to the disinfectant schedule with the illumination intensities and/or durations for the determined category of the one or more items and/or determined duration for the second route.

16. The non-transitory machine-readable storage medium of claim 15, wherein the engaging the one or more disinfecting systems is performed according to the disinfectant schedule that is further based on automatically identifying one or more surface materials, of the one or more items, by:
capturing one or more images of the one or more items, using one or more cameras directed toward the interior of the secured container; and
applying a machine learning model trained to produce surface material determinations.

17. The non-transitory machine-readable storage medium of claim 15, wherein the engaging the one or more disinfecting systems is performed according to the disinfectant schedule and wherein the process further comprises:
determining the disinfectant schedule is not complete prior to arriving at the delivery location; and
delaying unlocking a locking mechanism of the secured container until the disinfectant schedule is complete.

18. The non-transitory machine-readable storage medium of claim 15,
wherein the disinfecting systems include one or more ultraviolet (UV) lights; and
wherein the engaging the one or more ultraviolet (UV) lights is based on correlations of A) UV illumination intensities and/or durations to B) one or more categories assigned to the one or more items and/or one or more surface materials of the one or more items.

19. The non-transitory machine-readable storage medium of claim 15,
wherein the drop-off location is an intermediate location;
wherein obtaining the transportation parameters comprises determining a weight and/or dimensions of the one or more items; and
wherein, based on the determined weight and/or dimensions, the second route is a route to the intermediate location at which the one or more items are transferred to a second drone to transport the one or more items to the delivery location.

20. The non-transitory machine-readable storage medium of claim 15, wherein the drone is a flying drone and wherein the second route includes a flight route and flight time of the drone.

* * * * *